United States Patent
Mitchell

(10) Patent No.: US 6,845,063 B2
(45) Date of Patent: Jan. 18, 2005

(54) ELECTRONIC MEDICAL EMERGENCY VOICE BRACELET SYSTEM

(76) Inventor: Sherwin Mitchell, 2649 Bvron Pl., Los Angeles, CA (US) 90046

( * ) Notice: Subject to any disclaimer, the term of this patent is extended or adjusted under 35 U.S.C. 154(b) by 540 days.

(21) Appl. No.: 09/765,002

(22) Filed: Jan. 18, 2001

(65) Prior Publication Data

US 2002/0092220 A1 Jul. 18, 2002

(51) Int. Cl.[7] .................. G04B 47/00; G04B 21/08; G08B 23/00
(52) U.S. Cl. .................. 368/10; 368/63; 340/573.1; 340/573.3
(58) Field of Search .................. 340/573.3, 825.34, 340/573.1, 539, 572.8, 571; 368/10, 63, 72–74, 250, 251, 276, 281, 282; 235/492, 487

(56) References Cited

U.S. PATENT DOCUMENTS

| | | | |
|---|---|---|---|
| 4,406,549 A | 9/1983 | Takahashi | |
| 4,508,457 A | 4/1985 | Aizawa | |
| 5,012,229 A | 4/1991 | Lennon | |
| 5,086,391 A * | 2/1992 | Chambers | 364/413.02 |
| 5,088,037 A * | 2/1992 | Battaglia | 364/413.02 |
| 5,208,449 A | 5/1993 | Eastman | |
| 5,226,090 A | 7/1993 | Kimura | |
| 5,337,290 A | 8/1994 | Ventimiglia et al. | |
| 5,444,673 A | 8/1995 | Mathurin | |
| 5,877,742 A | 3/1999 | Klink | |
| 5,883,576 A * | 3/1999 | De La Huerga | 340/573.1 |
| 6,140,936 A * | 10/2000 | Armstrong | 340/825.34 |
| 6,220,916 B1 * | 4/2001 | Bart et al. | 446/26 |
| 6,419,158 B2 * | 7/2002 | Hoogland | 235/492 |

* cited by examiner

Primary Examiner—Vit W. Miska
(74) Attorney, Agent, or Firm—Birch, Stewart, Kolasch & Birch, LLP; Sanford Astor

(57) ABSTRACT

An audible medical emergency system for a patient comprising a bracelet which is battery operated and is worn on patient. The bracelet contains about 60 seconds of audible information about the wearer's health, including warnings about allergies to drugs, medical conditions, doctor's name and phone number, health insurance infomation, next of kin, etc. Information is loaded by computer onto a chip in the bracelet. When a button is pressed, a paramedic or doctor or anyone rendering assistance can listen to the information to aid in helping the wearer in an emergency. The information repeats by pushing the button again after it has played. The medical information is entered into a computer from information provided by the wearer and the computer loads the chip or disk in about two seconds. The audio is in a computer generated voice, so that the audio is quite clear.

7 Claims, 3 Drawing Sheets

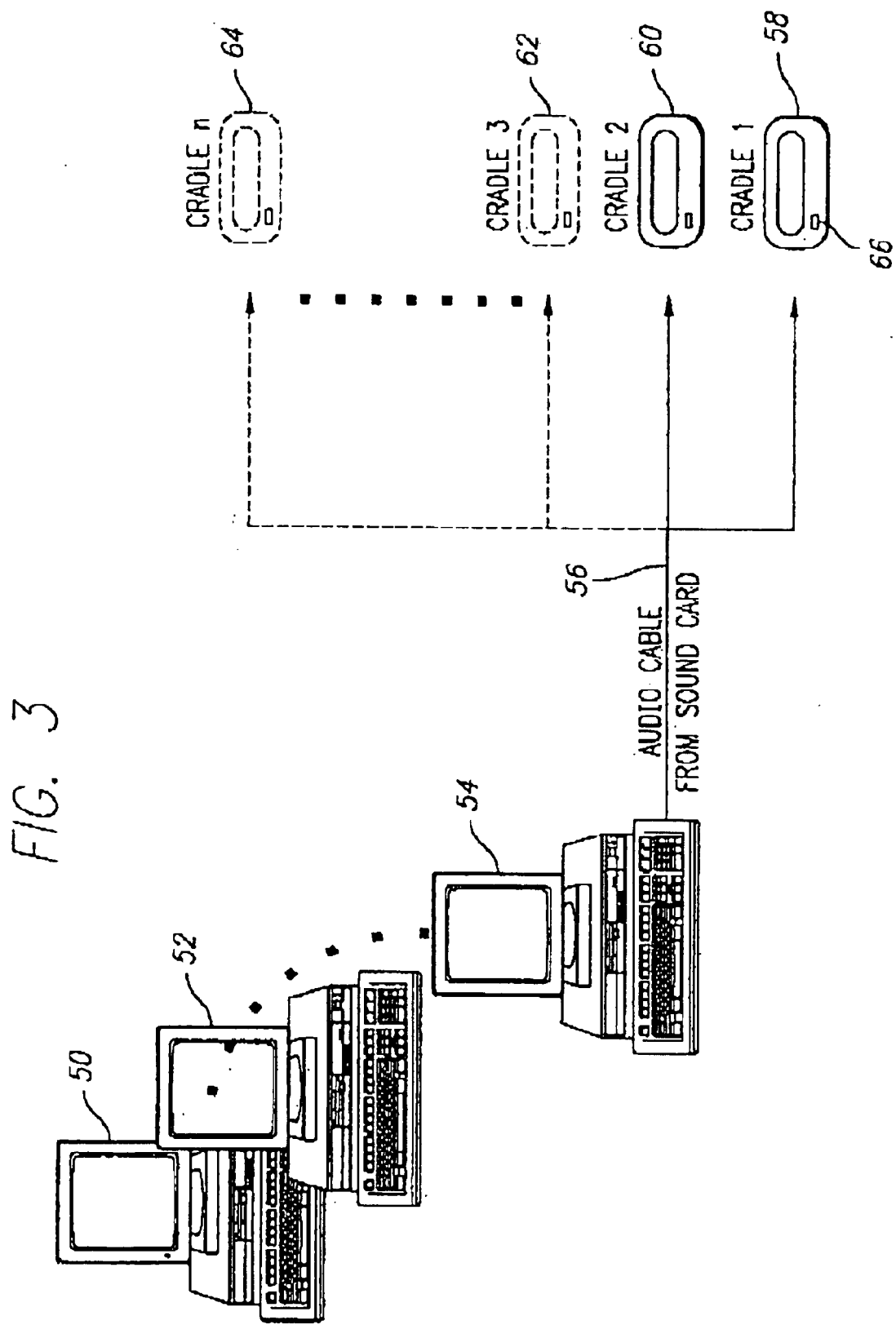

ELECTRONIC MEDICAL EMERGENCY VOICE BRACELET SYSTEM

BACKGROUND OF THE INVENTION

Millions of people who have a serious illness, take medication, or suffer from environmental or drug allergies are at serious risk if they should need medical assistance and are unable to speak for themselves. The simple medical bracelet has been used for some time to provide a warning to emergency medical personnel of some limited information. It can only provide hoever, a very small amount of information.

Other devices, such as the Health Watch described in U.S. Pat. No. 5,337,290, to Ventimiglia et al, have been suggested to provide emergency medical information. This device, however, suffers from several problems. It is too complex, having a number of "modes" that must be accessed to reach the information needed. It would require a skilled operator to access the information. It is also solely a visual device, in which the information has to be read on a very small screen. There could be many circumstances where it is not possible to read the information, depending on lighting, position, or other factors.

Another device is disclosed in U.S. Pat. No. 5,444,673, to Mathurin, which is described as an audio controlled and activated wristwatch memory and device. This device, while audio, is used to record meetings, tasks, etc. similar to a handheld recorder. The face of the device is quite complex and the information is input verbally to a recorder. This device is not suitable for Applicant's purposes for several reasons. The emergency medical information contained in Applicant's device is input by a computer. The patient, wearer, completes a form on which he or she sets forth all relevant medical information. That information is then input to a computer which loads the information onto a recordable chip. The information cannot be changed by the patient, and it would be dangerous to allow the patient to record the information and change it if he or she desired. It is also loaded in a computer generated voice, which is much clearer than a person's voice, which may have accent's, etc. Also, Applicant's device is very small, compared to the Manthurin device and easily wearable at all times, because one would not want to be wearing the Manthurin device for any length of time, due to its size.

SUMMARY OF THE INVENTION

The audio medical emergency bracelet of the present invention acts only audibly. The important medical information for any individual is entered into the device and it is played audibly by the push of only one button. It contains approximately one minute of audio to provide whatever information is necessary to warn the health care provider. The button can simply be pressed a second, third or more times to replay the information or to play it for other providers.

Examples of the medical information provided audibly by the device are: medications and dosage, chronic illnesses, environmental and drug allergies, diabetes and insulin dosage, high blood pressure, doctor's name and number, next of kin and other critical health information.

The audio play of the bracelet can be heard above the noise of an accident scene. It can also alert the emergency medical personnel to search the wearer's wallet for a medical card or insurance information.

OBJECTS OF THE INVENTION

Accordingly, several objects and advantages of the invention are as follows:

It is an object of the present invention to provide an audio medical information bracelet which may be worn by the patient at all times.

Another object of the invention is to provide such a bracelet into which emergency medical information may be stored by computer and accessed by the push of one button.

Yet another object of the invention is to provide such a bracelet which is small in size and weight, so that the patient is not inconvenienced by wearing it.

These, and other objects of the invention will become apparant from the following description and drawings.

BRIEF DESCRIPTION OF THE DRAWINGS

FIG. 3 is a diagrammatic view of the input of the information.

DETAILED DESCRIPTION OF THE INVENTION

Figure 1:
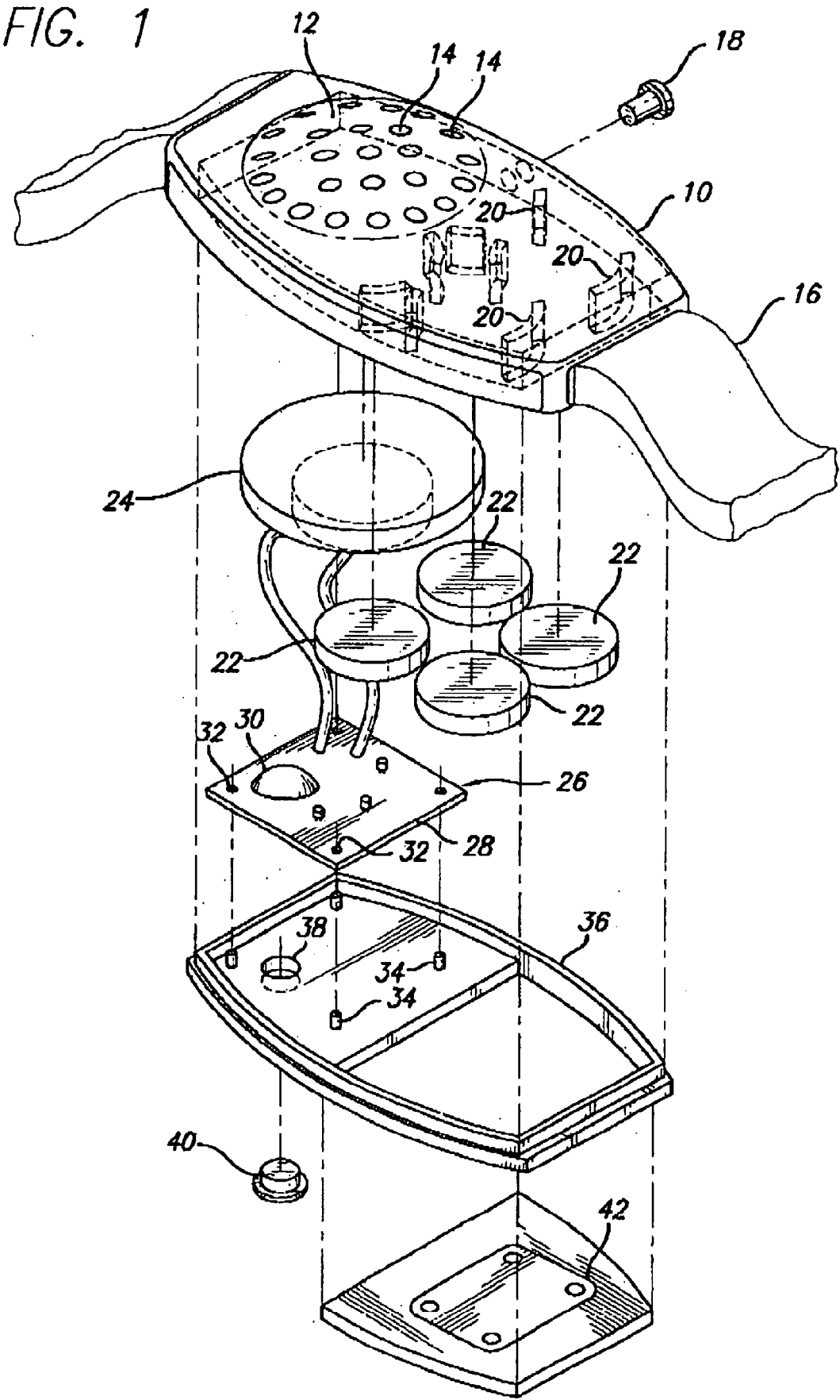
FIG. 1 is an exploded perspective view of the bracelet of this invention.
Figure 2:
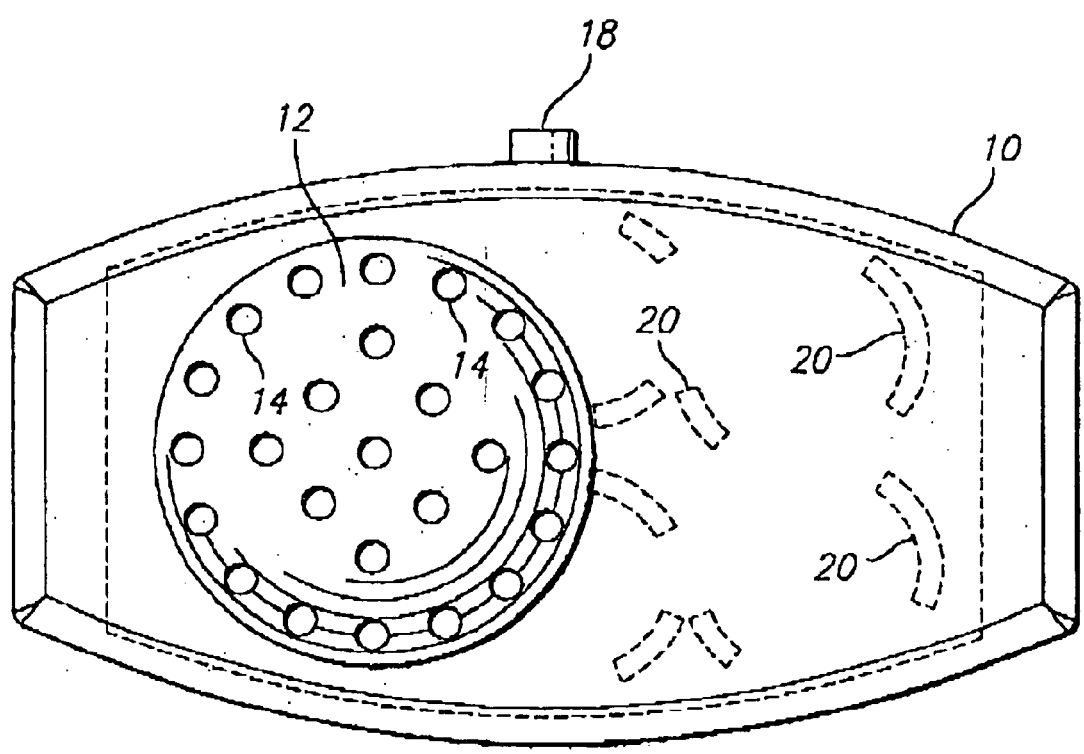
FIG. 2 is a top plan view.

Referring now to the drawings, there is shown the bracelet upper cover 10 having a speaker cover 12 with holes 14 to allow the audio to be heard. Band 16 is worn around the wrist, arm, or other location on the body.

Button switch 18 actuates the play of the audio recording. A plurality of battery holders 20 hold one or more standard, circular, button batteries 22 to power the unit. Speaker 24 fits under speaker cover 12.

PCB board 26 comprises breadboard 28 and chip 30, which provide the means to record and play audio voice recordings. Breadboard 28 is held in place by holes 32 which fit onto pegs 34 affixed to lower cover 36. Hole 38 through lower cover 36 provides access for connection of a cable from a computer 54 to a connection under PCB board 26, to load the information which will be audibly broadcast when button 18 is pushed. Plug 40 closes hole 38 when not in use. Door 42 provides access to change batteries 22.

FIG. 3 depicts computers 50 and 52, into which medical information for the patient is entered. Programs which may be used to enter the patient medical information include Word, Word Perfect, or any other word processing program. This information is then transferred to computer 54 which has a program to transfer the information from the computer onto chip 30 in the bracelet.

The information is transferred by audio cable 56 from a sound card in computer 54. The bracelet is set into a cradle 58 and the information transfer is made, in about two seconds. Computer 54 may transfer information to a plurality of cradles 58, 60, 62, 64, simultaneously, by use of an audio cable attached to each cradle. Each bracelet receives information for a particular patient. Each cradle has an on-off switch.

Bracelet 10 can have a water-proof cover over the speaker cover 12 so that the bracelet can be worn in a shower or pool. The batteries utilized are standard button batteries, such as A76 1.5 volt batteries. Recordable chip 30 is a standard audio chip such as an APR9301 chip manufactured by A PLUS, Inc., and will play for about 100 plays before new batteries are needed. Chip 30 holds about one minute of audible information.

Covers 10 and 36 can be made of any convenient material, preferable plastic, but could be made of a metal. When made of plastic, the covers can come in many different colors.

Having thus described the invention,
I claim:

1. A system to provide audio delivered emergency medical information carried on a patient's person comprising a battery operated audible medical bracelet having an upper speaker cover, a lower battery access cover, a plurality of batteries to provide power, a re-recordable chip which holds medical information adapted to be played audibly, said chip connected to a speaker affixed below the speaker cover, which speaker audibly plays the medical information, a switch to initiate the audible information, means to enter the medical information into a computer via a word processing program, computer program means to convert the medical information to a sound file, means to transfer the sound file from the computer to the chip in the bracelet, means to access said chip while in said bracelet to re-record new medical information on said chip.

2. The system of claim 1 further comprising a wrist band.

3. The system of claim 1 in which the audio information is a computer generated voice.

4. The system of claim 1 in which the information is actuated by one push of the switch.

5. The system claim 1 in which the audio information comprises illnesses, allergies, doctor's name and number, next of kin's name and number, and other medical information.

6. The system of claim 1 further comprising a waterproof cover over the speaker.

7. The system of claim 1 further comprising cover means to cover the access to said chip.

* * * * *